United States Patent
Ebinuma et al.

(10) Patent No.: US 10,626,452 B2
(45) Date of Patent: Apr. 21, 2020

(54) METHOD FOR DETECTING SINGLE BASE SUBSTITUTION USING ION-EXCHANGE CHROMATOGRAPHY

(71) Applicant: SEKISUI MEDICAL CO., LTD., Tokyo (JP)

(72) Inventors: Hiroyuki Ebinuma, Tokyo (JP); Katsura Uchida, Tokyo (JP); Yuriko Tsukamoto, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 16/325,605

(22) PCT Filed: Sep. 29, 2017

(86) PCT No.: PCT/JP2017/035441
§ 371 (c)(1),
(2) Date: Feb. 14, 2019

(87) PCT Pub. No.: WO2019/064483
PCT Pub. Date: Apr. 4, 2019

(65) Prior Publication Data
US 2019/0203284 A1 Jul. 4, 2019

(51) Int. Cl.
*C12Q 1/6858* (2018.01)
*G01N 30/96* (2006.01)
*C12Q 1/6827* (2018.01)
*C12N 15/09* (2006.01)

(52) U.S. Cl.
CPC .......... *C12Q 1/6858* (2013.01); *C12N 15/09* (2013.01); *C12Q 1/6827* (2013.01); *G01N 30/96* (2013.01)

(58) Field of Classification Search
CPC ........ C12Q 2535/125; C12Q 2565/137; C12Q 1/6858
See application file for complete search history.

(56) References Cited

U.S. PATENT DOCUMENTS

| 6,210,885 B1 * | 4/2001 | Gjerde | C12Q 1/6816 210/198.2 |
|---|---|---|---|
| 9,447,460 B2 | 9/2016 | Yotani et al. | |
| 2014/0147842 A1 | 5/2014 | Yotani et al. | |
| 2014/0349284 A1 | 11/2014 | Yotani et al. | |
| 2015/0197795 A1 | 7/2015 | Yotani et al. | |

FOREIGN PATENT DOCUMENTS

| JP | 2005-323565 A | 11/2005 |
|---|---|---|
| JP | 2009-125020 A | 6/2009 |
| JP | 2010-35532 A | 2/2010 |
| WO | WO 02/46393 A1 | 6/2002 |
| WO | WO 2009/132860 A1 | 11/2009 |
| WO | WO 2012-096329 A1 | 7/2012 |
| WO | WO 2012/133834 A1 | 10/2012 |
| WO | WO 2017/170101 A1 | 10/2017 |

OTHER PUBLICATIONS

International Preliminary Report on Patentability for PCT/JP2017/011644 dated Dec. 26, 2017.
International Search Report for PCT/JP2017/011644 dated Jun. 27, 2017.
International Search Report for PCT/JP2017/035441 (PCT/ISA/210) dated Dec. 26, 2017.
Oefner et al., "High-Resolution Liquid Chromatography of Fluorescent Dye-Labeled Nucleic Acids", Analytical Biochemistry, 1994, vol. 223, No. 1, pp. 39-46.
Takei et al., "Detection of MPLW515L/K Mutations and Determination of Allele Frequencies with a Single-Tube PCR Assay", PLOS ONE, Aug. 21, 2014, vol. 9, No. 8, e104958, total 8 pages.
Written Opinion of the International Searching Authority for PCT/JP2017/035441 (PCT/ISA/237) dated Dec. 26, 2017.

* cited by examiner

*Primary Examiner* — Teresa E Strzelecka
(74) *Attorney, Agent, or Firm* — Birch, Stewart, Kolasch & Birch, LLP

(57) ABSTRACT

An object of the present invention is to provide a method for accurately and quantitatively discriminating and detecting a wide variety of gene mutations, or particularly, single base substitutions or point mutations. In an ASP for analyzing gene mutations, or particularly, single base substitutions or point mutations, when a non-nucleotide component is added to the 5' end of at least one of the ASP and a primer paired therewith before amplification by PCR and amplification products thereof are separated by ion-exchange chromatography, even the amplification products having the same length can be separated and detected.

15 Claims, 2 Drawing Sheets
Specification includes a Sequence Listing.

[FIG.1]
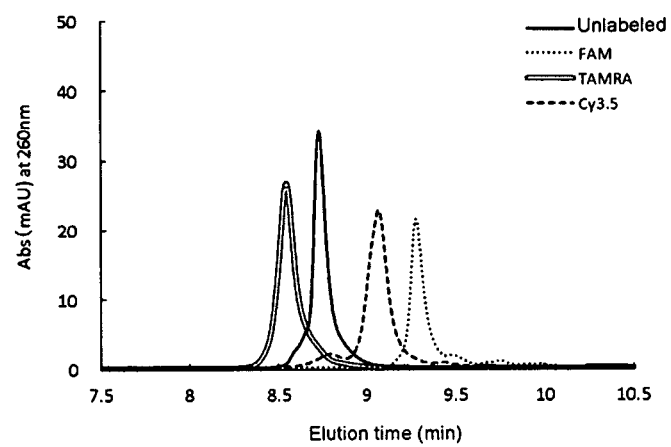
[FIG.2]
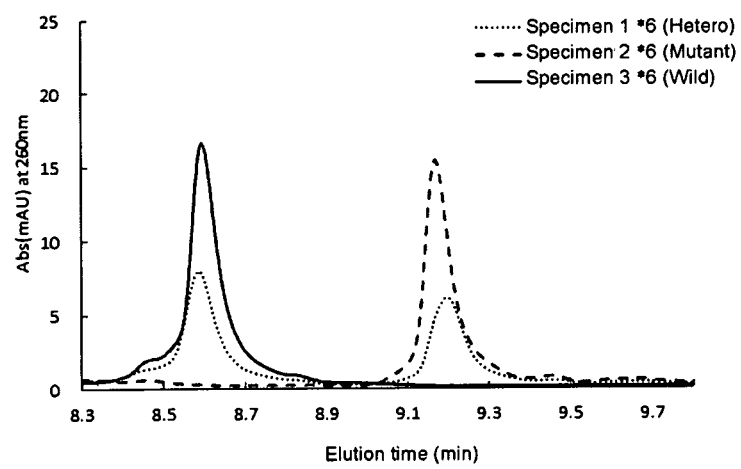

[FIG.3]
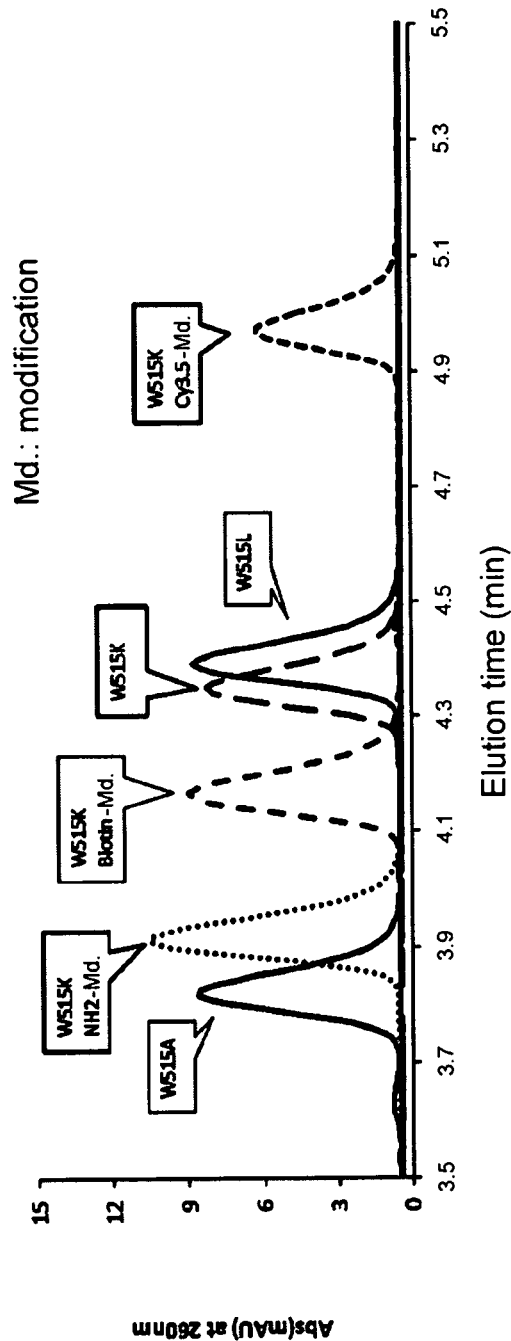

METHOD FOR DETECTING SINGLE BASE SUBSTITUTION USING ION-EXCHANGE CHROMATOGRAPHY

TECHNICAL FIELD

The present invention relates to a method for specifically detecting a mutation such as a single base substitution or a point mutation contained in a nucleic acid sample.

BACKGROUND ART

Genetic mutations include genetically inherited germline mutation and somatic mutation that is acquired mutation induced in each cell, and it is reported that a specific genotype of a single nucleotide polymorphisms (SNP) of a specific gene in the germline mutation and somatic mutation such as point mutation (single base substitution), insertion, and deletion are associated with various diseases, and in recent years, identification of base sequences thereof is used for screening patients for which a specific drug is expected to be effective. For example, genetic polymorphism of UGT1A1 is used for judging a risk of occurrence of serious side effects of irinotecan, an anticancer agent. In a UGT1A1 genetic polymorphism test, it must be determined whether each of two base sequences (*6, *28) is the wild type without mutation, a heterozygote having both the wild type and the mutated forms, or a homozygote having only the mutated form. A JAK2 gene mutation used for diagnosing polycythemia vera, one of genetic mutations of myeloid proliferative diseases, is a gain-of-function acquired somatic mutation and is a point mutation of 1849 G>T of exon 14, resulting in constitutive activation of receptor tyrosine kinase. Since the detection of existence as well as quantitative changes of this point mutation has clinical utility, it is required to calculate an allele frequency. Therefore, as in genetic polymorphism detection, both the mutated form and the wild type must quantitatively be detected in point mutation detection. Additionally, the MPL (myeloproliferative leukemia virus) gene mutation set as World Health Organization (WHO) diagnostic criteria for primary myelofibrosis includes point mutations and deletion/insertion mutations at the 1543rd to 1544th bases of codon 515 of exon 10 and therefore has several mutation patterns at the same positions, and these patterns are desirably detected in a distinguished manner.

Ion-exchange chromatography is used as a method capable of accurately separating and detecting nucleic acid in a short time. An advantage of applying ion-exchange chromatography to detection of nucleic acid is that since nucleic acid can be separated according to the chain length thereof, multiple amplification products can be separated and detected in a single measurement by adjusting the length of the amplification products resulting from PCR (polymerase chain reaction), for example. Although this principle can theoretically be applied to the detection of multiple gene mutations as described above, ingenuity is required for detection of a slight difference of one base such as a single base substitution or a point mutation. In the case of single base substitution detection, even if primers for PCR are simply designed to bracket SNP sites to obtain amplification products, it is difficult to separate the difference of a single base by ion-exchange chromatography. In this regard, Patent Document 1 discloses a method for separating and detecting SNP with ion-exchange chromatography by adding to the 5' end of an allele specific primer (ASP) a sequence (tag sequence) incompletely complementary to the template DNA, and thereby, artificially changing the length of amplification products resulting from PCR. However, if the added base sequence is too long, Tm value for primers significantly changes, so that specificity may no longer be maintained. Conversely, if the sequence is too short, a reduced difference in amplification product length leads to poor separation by ion-exchange chromatography, and it is concerned that single nucleotide polymorphism cannot accurately be determined.

On the other hand, it is reported that separation using capillary electrophoresis can be achieved by designing ASPs at the forward and the reverse sides on the double strand and by designing primers paired therewith in appropriate places other than the mutation site to obtain two kinds of amplification products having different sizes (Non-Patent Document 1). However, in this method, the primers irrelevant to mutation are paired with each other and allow amplification to proceed, so that components required for amplification are consumed, which may affect a specific reaction. Furthermore, since two pairs of paired primers are used, the efficiency of hybridization and amplification is prone to vary, which makes it difficult to accurately calculate an allele frequency when a gene mutation such as JAK2 gene mutation is detected. Additionally, this method is limited to detection of two kinds of mutations and cannot be applied to a large variety of mutations such as multiple mutations around codon 515 of MPL and point mutations of codon 12 and codon 13 of KRAS, NRAS, etc.

CITATION LIST

Patent Literature

Patent Document 1: WO2012/133834

Non Patent Literature

Non-Patent Document 1: Takei H, Morishita S, Araki M, Edahiro Y, Sunami Y, Hironaka Y, Noda N, Sekiguchi Y, Tsuneda S, Ohsaka A, Komatsu N. Detection of MPLW515L/K mutations and determination of allele frequencies with a single-tube PCR assay. PLoS One. 2014 Aug. 21; 9(8):e104958.

SUMMARY OF INVENTION

Technical Problem

In view of the conventional problems as described above, an object of the present invention to provide a method for accurately and quantitatively discriminating and detecting a wide variety of gene mutations, or particularly, single base substitutions or point mutations.

Solution to Problem

For a means for solving the problems, it has been found that when using an ASP for analyzing gene mutations, or particularly, single base substitutions or point mutations, if a non-nucleotide component is added to the 5' end of at least one of the ASP and a primer paired therewith before amplification by PCR and amplification products thereof are separated by ion-exchange chromatography, even the amplification products having the same length can be separated and detected, and the present invention has been thereby completed. Therefore, the present invention has the following configurations [1] to [8].

[1]

A method for detecting a gene mutation comprising a step of discriminating, by using ion-exchange chromatography, two or more kinds of gene amplification products amplified by using two or more kinds of allele specific primers, characterized in that a non-nucleotide component is added to the 5' end of at least one of the two or more kinds of allele specific primers: wherein the non-nucleotide component is preferably an ionic functional group selected from the group consisting of a hydroxy group, an aldehyde group, a carboxy group, an amino group, a nitro group, a nitroso group, a thiol group, a sulfonic acid group, a fluoro group, a chloro group, a bromo group, and iodine group, or a molecule containing at least one or more of the ionic functional groups, more preferably a fluorescent substance described in Table 1, and a difference in size of the amplification products is 0 base pair, 1 base pair, 2 base pairs, 3 base pairs, 4 base pairs, 5 base pairs, 6 base pairs, 7 base pairs, 8 base pairs, 9 base pairs, or 10 base pairs, more preferably 0 base pair, 1 base pair, or 2 base pairs, further preferably 0 base pair.

[2]

The detection method according to [1] above, wherein the ion-exchange chromatography is anion-exchange chromatography.

[3]

The detection method according to [1] or [2] above, wherein the non-nucleotide component is a substance inducing a change in electric charge at the 5' end of the primer.

[4]

A method for detecting the presence of at least one allele at a polymorphic site contained in a double-stranded deoxyribonucleic acid in a sample, comprising the steps of:
  (a) providing a sample containing a double-stranded deoxyribonucleic acid containing a polymorphic site;
  (b) providing a first primer, a second primer, and a third primer, wherein
  the sequence of the first primer is complementary to the second strand of the double-stranded deoxyribonucleic acid having a first allele at the polymorphic site, and any one or two or three out of three bases at the 3' end or one or both of two bases at the 3' end of the sequence of the first primer corresponds to the polymorphism site, wherein
  the sequence of the second primer is complementary to the second strand of the double-stranded deoxyribonucleic acid having a second allele at the polymorphic site, and any one or two or three out of three bases at the 3' end or one or both of two bases at the 3' end of the sequence of the second primer corresponds to the polymorphism site, wherein
  the sequence of the third primer does not include the polymorphic site and is complementary to the first strand of the double-stranded deoxyribonucleic acid, wherein
  a non-nucleotide component is added to at least one of the first primer and the second primer, wherein
  the non-nucleotide component is preferably an ionic functional group selected from the group consisting of a hydroxy group, an aldehyde group, a carboxy group, an amino group, a nitro group, a nitroso group, a thiol group, a sulfonic acid group, a fluoro group, a chloro group, a bromo group, and iodine group, or a molecule containing at least one or more of the ionic functional groups, more preferably a fluorescent substance described in Table 1;
  (c) performing a polymerase chain reaction, wherein
  the polymerase chain reaction is performed under a condition that strand elongation due to a polymerase from the first primer hybridized to the second strand of the double-stranded deoxyribonucleic acid having the first allele preferentially occurs as compared to strand elongation due to a polymerase from the second primer hybridized to the second strand of the double-stranded deoxyribonucleic acid having the first allele, and that strand elongation due to a polymerase from the second primer hybridized to the second strand of the double-stranded deoxyribonucleic acid having the second allele preferentially occurs as compared to strand elongation due to a polymerase from the first primer hybridized to the second strand of the double-stranded deoxyribonucleic acid having the second allele;
  (d) subjecting amplification products of the polymerase chain reaction to ion-exchange chromatography; wherein the ion-exchange chromatography is preferably anion-exchange chromatography, wherein
  the difference in size of the amplification product of the polymerase chain reaction from the first primer and the third primer and the amplification product of the polymerase chain reaction from the second primer and the third primer is 0 base pair, 1 base pair, 2 base pairs, 3 base pairs, 4 base pairs, 5 base pairs, 6 base pairs, 7 base pairs, 8 base pairs, 9 base pairs, or 10 base pairs, more preferably 0 base pair, 1 base pair, or 2 base pairs, further preferably 0 base pair; and
  (e) detecting the presence of one or both of the first and second alleles based on elution positions or elution times of the amplification products.

[5]

The method according to [4] above, wherein the step (a) is a step of extracting genomic DNA from a somatic cell specimen of mammals such as human.

[6]

The method according to [4] or [5] above, wherein the polymorphic site is a UGT1A1*28 polymorphism (rs8175347), a UGT1A1*6 polymorphism (rs4148323), a JAK2 1849G>T (V617F) mutation site (rs77375493), an MPL 1589G>T (W515L) mutation site (rs121913615), or an MPL 1588:1599TG>AA (W515K) mutation site (rs121913616).

[7]

The method according to any one of [4] to [6] above, wherein the non-nucleotide component is a substance inducing a change in electric charge at the 5' end of the primer.

[8]

The method according to any one of [4] to [7] above, wherein the non-nucleotide component is added to the third primer, wherein
  the non-nucleotide component is preferably an ionic functional group selected from the group consisting of a hydroxy group, an aldehyde group, a carboxy group, an amino group, a nitro group, a nitroso group, a thiol group, a sulfonic acid group, a fluoro group, a chloro group, a bromo group, and iodine group, or a molecule containing at least one or more of the ionic functional groups, more preferably a fluorescent substance described in Table 1.

Advantageous Effects of Invention

In the case of ASPs for analyzing single base substitutions or point mutations, amplification products have the same length or may have differences of 1 to 2 bases depending on the sequence and are generally difficult to separate and detect with ion-exchange chromatography.

In this regard, when a non-nucleotide component is added to the 5' end of at least one of the ASP and a primer paired therewith before amplification by PCR, the amplification product is labeled with one or two non-nucleotide components. It is presumed that this small differences in the physical properties and the number of labels slightly change the ionic strength of the amplification product and changes the elution position in ion-exchange chromatography, thereby enabling the separation and detection of the amplification product by using this characteristic.

DESCRIPTION OF EMBODIMENTS

An allele-specific primer used in the present invention may be any primer capable of specifically binding to a base sequence of genetic polymorphism or gene mutation, and any primers are usable without particular limitation as long as the primers are specific to e.g., a base sequence containing single base substitutions, insertion or deletion mutations and applicable to separation according to the present invention.

The non-nucleotide component used in the present invention is preferably a substance inducing a change in electric charge at the 5' end of the primer and is not particularly limited as long as a change in elution pattern occurs when a gene amplification product amplified by using the allele specific primer having the component added thereto is analyzed or distinguished by using ion-exchange chromatography. Preferable examples of the non-basic substances include an ionic functional group itself or a molecule containing at least one or more ionic functional groups. The ionic functional group is not particularly limited, and examples thereof include a hydroxy group, an aldehyde group, a carboxy group, an amino group, a nitro group, a nitroso group, a thiol group, a sulfonic acid group, a fluoro group, a chloro group, a bromo group, and iodine group. A fluorescent dye used for modifying a primer can also be used as the non-nucleotide component, and examples thereof include the Alexa Fluor series, the Cy series, the ATTO series, the DY series, the DyLight series, FAM, TAMRA, etc. Additionally, addition of functional substances such as digoxin (DIG) and biotin, amide group modification, etc. can also be used without limitation. Examples of the fluorescent dye usable as the non-nucleotide component are described in Table 1.

The effects of these modifying substances are further enhanced by optimizing the length of a gene amplification product amplified by using the allele specific primer. Specifically, even the same modifying substance causes a difference more prominently when the length of the gene amplification product is shorter. Therefore, in the present invention, when a gene amplification product amplified by using the allele-specific primer having the non-nucleotide component added at the 5' end is analyzed or distinguished by using ion-exchange chromatography, the effects of the present invention can be maximized not only according to the type of the non-nucleotide component but also by appropriately combining with the length of the gene amplification products.

TABLE 1-1

| Product name | Synonym | IUPAC name | Canonical SMILES/Isomeric SMILES |
|---|---|---|---|
| 5-FAM | 5-Carboxyfluorescein | 3',6'-dihydroxy-3-oxospiro[2-benzofuran-1,9'-xanthene]-5-carboxylic acid | C1=CC2=C(C=C1C(=O)O)C(=O)OC23C4=C(C=C(C=C4)O)OC5=C3C=CC(=C5)O |
| 5-ROX | 5-carboxy-X-rhodamine | 16-(2-carboxy-4-carboxylatophenyl)-3-oxa-9 $\lambda^6$,23-diazaheptacyclo [17.7,1.1$^{5,9}$.0$^{2,17}$.0$^{4,15}$.0$^{22,27}$.0$^{13,28}$] octacosa-1,4,9(28),13,15,17,19(27)-heptaen-9-ylium | C1CC2=C3C(=C4C(=C2)C(=C5C=C6CCC[N+]7=C6C(=C5O4)CCC7)C8=C(C=C(C=C8)C(=O)[O-])C(=O)O)CCCN3C1 |
| 6-FAM | 6-Carboxyfluorescein | 3',6'-dihydroxy-1-oxospiro[2-benzofuran-3,9'-xanthene]-5-carboxylic acid | C1=CC2=C(C=C1C(=O)O)C3(C4=C(C=C(C=C4)O)OC5=C3C=CC(=C5)O)OC2=O |
| 6-JOE | 6-carboxy-4',5'-dichloro-2',7'-dimethoxyfluorescein | 4',5'-dichloro-3',6'-dihydroxy-2',7'-dimethoxy-1-oxospiro[2-benzofuran-3,9'-xanthene]-5-carboxylic acid | COC1=C(C(=C2C(=C1)C3(C4=CC=C(C(=C4O2)Cl)O)OC)C5=C(C=CC(=C5)C(=O)O)C(=O)O3)Cl)O |
| 6-ROX | 6-Carboxy-X-rhodamine | 16-(2-carboxy-5-carboxylatophenyl)-3-oxa-9 $\lambda^5$,23-diazaheptacyclo [17.7,1.1$^{5,9}$.0$^{2,17}$.0$^{4,15}$.0$^{22,27}$.0$^{13,23}$] octacosa-1,4,9(28),13,15,17,19(27)-heptaen-9-ylium | C1CC2=C3C(=C4C(=C2)C(=C5C=C6CCC[N+]7=C6C(=C5O4)CCC7)C8=C(C=CC(=C8)C(=O)[O-])C(=O)O)CCCN3C1 |
| 6-TET | 6-carboxy-2',4,7,7'-tetrachlorofluorescein succinimiylester | (2,5-dioxopyrrolidin-1-yl) 2',4,7,7'-tetrachloro-3',6'-dihydroxy-1-oxospiro[2-benzofuran-3,9'-xanthene]-5-carboxylate | C1CC(=O)N(C1=O)OC(=O)C2=CC(=C3C(=C2Cl)C4(C5=CC(=C(C=C5OC6=CC(=C(C=C64)Cl)O)O)Cl)OC3=O)Cl |
| Alexa Fluor 350 | 7-amino-4-methyl-6-sulfocoumarin-3-acetic acid | 7-amino-3-[2-(2,5-dioxopyrrolidin-1-yl)oxy-2-oxoethyl]-4-methyl-2-oxochromene-6-sulfonic acid | CC1=C(C(=O)OC2=CC(=C(C=C12)S(=O)(=O)O)N)CC(=O)ON3C(=O)CCC3=O |
| Alexa Fluor 430(1-) | N/A | [9-[6-(2,5-dioxopyrrolidin-1-yl)oxy-6-oxohexyl]-8,8-dimethyl-2-oxo-4-(trifluoromethyl)pyrano[3,2-g]quinolin-6-yl] methanesulfonate | CC1(C=C(C2=C(N1CCCCCC(=O)ON3C(=O)CCC3=O)C=C4C(=C2)C(=CC(=O)O4)C(F)(F)F)CS(=O)(=O)[O-])C |
| Alexa Fluor 480(3-) | N/A | 3-(3-amino-6-imino-4,5-disulfonatoxanthen-9-yl)-4-carboxybenzoate | C1=CC(=C(C=C1C(=O)[O-])C2=C3C=CC(=N)C(=C3OC4=C2C=CC(=C4S(=O)(=O)[O-])N)S(=O)(=O)[O-])C(=O)O |
| Alexa Fluor 488 meta-isomer | dilithium 5-carboxy-2-(3,6-diamino-4,5-disulfonatoxanthenium-9-yl)benzoate | dilithium;3-amino-9-(2,4-dicarboxyphenyl)-6-iminoxanthene-4,5-disulforiate | [Li+].[Li+].C1=CC(=C(C=C1C(=O)O)C(=O)O)C2=C3C=CC(=N)C(=C3OC4=C2C=CC(=C4S(=O)(=O)[O-])N)S(=O)(=O)[O-] |
| Alexa Fluor 488 meta-isomer(2-) | 5-carboxy-2-(3,6-diamino-4,5-disulfonatoxanthenium-9-yl)benzoate | 3-amino-9-(2,4-dicarboxyphenyl)-6-iminoxanthene-4,5-disulfonate | C1=CC(=C(C=C1C(=O)O)C(=O)O)C2=C3C=CC(=N)C(=C3OC4=C2C=CC(=C4S(=O)(=O)[O-])N)S(=O)(=O)[O-] |

TABLE 1-1-continued

| Product name | Synonym | IUPAC name | Canonical SMILES/Isomeric SMILES |
|---|---|---|---|
| Alexa Fluor 488 para-isomer | dilithium 4-carboxy-2-(3,6-diamino-4,5-disulfonatoxanthenium-9-yl)benzoate | dilithium;3-amino-9-(2,5-dicarboxyphenyl)-6-iminoxanthene-4,5-disulfonate | [Li+].[Li+].C1=CC(=C(C=C1C(=O)O)C(=O)O)C2=C3C=CC(=N)C(=C3OC4=C2C=CC(=C4S(=O)(=O)[O-])N)S(=O)(=O)[O-] |
| Alexa 488 para-isomer(2-) | 4-carboxy-2-(3,6-diamino-4,5-disulfonatoxanthenium-9-yl)benzoate | 3-amino-9-(2,5-dicarboxyphenyl)-6-iminoxanthene-4,5-disulfonate | C1=CC(=C(C=C1C(=O)O)C2=C3C=CC(=N)C(=C3OC4=C2C=CC(=C4S(=O)(=O)[O-])N)S(=O)(=O)[O-])C(=O)O |
| Alexa Fluor 514 meta-isomer | 6-(2-carboxy-4-{[(2,5-dioxopyrrolidin-1-yl)oxy]carbonyl}phenyl)-9-iminio-2,2,4-trimethyl-12-sulfo-1,3,4,9-tetrahydro-2H-chromeno[3,2-g]quinoline-10-sulfonate | 9-amino-6-[2-carboxy-4-(2,5-dioxopyrralidin-1-yl)oxycarbonylphenyl]-2,2,4-trimethyl-12-sulfo-3,4-dihydrochromeno[3,2-g]quinolin-1-ium-10-sulfonate | CC1CC([NH+]=C2C1=CC3=C(C4=C(C=C(C=C4)N)S(=O)(=O)[O-])OC3=C2S(=O)(=O)O)C5=C(C=CC(=C5)C(=O)ON6C(=O)CCC6=O)C(=O)O)(C)C |
| Alexa Fluor 514 para-isomer | 6-(2-carboxy-5-{[(2,5-dioxopyrrolidin-1-yl)oxy]carbonyl}phenyl)-9-iminio-2,2,4-trimethyl-12-sulfo-1,3,4,9-tetrahydro-2H-chromeno[3,2-g]quinoline-10-sulfonate | 9-amino-6-[2-carboxy-4-(2,5-dioxopyrralidin-1-yl)oxycarbonylphenyl]-2,2,4-trimethyl-12-sulfo-3,4-dihydrochromeno[3,2-g]quinolin-1-ium-10-sulfonate | CC1CC([NH+]=C2C1=CC3=C(C4=C(C=C(C=C4)N)S(=O)(=O)[O-])OC3=C2S(=O)(=O)O)C5=C(C=CC(=C5)C(=O)ON6C(=O)CCC6=O)C(=O)O)(C)C |
| Alexa Fluor 532 | N/A | 12-(4-carboxyphenyl)-7,8,8,16.16,17-hexamethyl-4,20-disulfo-2-oxa-6, 18-diazapentacyclo[11.7.0.0$^{3,14}$.0$^{5,9}$,0$^{15,19}$]icosa-1(20),3,5,9,11,13,15(19)-heptaen-6-ium | CC1C(C2=C(N1)C(=C3C(=C2)C(=C4C=C5C(=[NH+]C(C5(C)C)C)C(=C4O3)S(=O)(=O)O)C6=CC=C(C=C6)C(=O)O)S(=O)(=O)O)(C)C |
| Alexa Fluor 546 | N/A | (2-{[4-carboxy-2,3,6-trichloro-5-(2,2,4,8,10.10-hexamethyl-12,14-disulfo-2,3,4,8,9,10-hexahydro-1H-13-oxa-1,11-diazapentacen-6-yl)phenyl]sulfanyl}-1-hydroxyethylidene)({6-[(2,5-dioxopyrrolidin-1-yl)oxy]-6-oxohexyl}azanium | CC1CC(NC2=C1C=C3C(=C4C=C5C(CC(N=C5C(=C4OC3=C2S(=O)(=O)S(=O)(=O)O)(C)C)C)C6=C(C(=C(C(=C6Cl)SCC(=[NH+]CCCCCC(=O)ON7C(=O)CCC7=O)O)Cl)Cl)C(=O)O)(C)C |
| Alexa Fluor 555 | N/A | 4-(3-amino-6-imino-4,5-disulfoxanthen-9-yl)benzene-1,3-dicarboxylic acid | C1=CC(=C(C=C1C(=O)O)C(=O)O)C2=C3C=CC(=N)C(=C3OC4=C2C=CC(=C4S(=O)(=O)O)N)S(=O)(=O)O |
| Alexa Fluor 568 ortho-isomer | [6-(2-carboxy-4-{[(2,5-dioxopyrrolidin-1-yl)oxy]carbonyl}phenyl)-2,2,10,10-tetramethyl-8-(sulfomethyl)-10,11-dihydro-2H-pyrano[3,2-g:5,6-g']diquinolin-1-ium-4-yl]methanesulfonate | [6-(2-carboxy-4-{[(2,5-dioxopyrrolidin-1-yl)oxy]carbonyl}phenyl)-2,2,10,10-tetramethyl-4(sulfomethyl)-8-(sulfonatomethyl)-2,10-dihydro-1H-13-oxa-1,11-diazapentacen-11-ium | CC1(C=C(C2=CC3=C(C=C2N1)OC4=CC5=[NH+]C(C=C(C5=CC4=C3C6=C(C=C(C=C6)C(=O)ON7C(=O)CCC7=O)C(=O)O)CS(=O)(=O)[O-])(C)C)CS(=O)(=O)O)C |
| Alexa Fluor 568 para-isomer | [6-(2-carboxy-5-{[(2,5-dioxopyrrolidin-1-yl)oxy]carbonyl}phenyl)-2,2,10,10-tetramethyl-8-(sulfomethyl)-10,11-dihydro-2H-pyrano[3,2-g:5,6-g']diquinolin-1-ium-4-yl]methanesulfonate | [6-(2-carboxy-4-{[(2,5-dioxopyrrolidin-1-yl)oxy]carbonyl}phenyl)-2,2,10,10-tetramethyl-4(sulfomethyl)-8-(sulfonatomethyl)-2,10-dihydro-1H-13-oxa-1,11-diazapentacen-11-ium | CC1(C=C(C2=CC3=C(C=C2N1)OC4=CC5=[NH+]C(C=C(C5=CC4=C3C6=C(C=CC(=C6)C(=O)ON7C(=O)CCC7=O)C(=O)O)CS(=O)(=O)[O-])(C)C)CS(=O)(=O)O)C |
| Alexa Fluor 594 meta-isomer | [6-(2-carboxy-4-{[(2,5-dioxopyrrolidin-1-yl)oxy]carbonyl}phenyl)-1,2,2,10,10,11-hexamethyl-8(sulfomethyl)-10,11-dihydro-2H-pyrano[3,2-g:5,6-g']diquinolin-1-ium-4-yl]methanesulfonate | [6-(2-carboxy-4-{[(2,5-dioxopyrrolidin-1-yl)oxy]carbonyl}phenyl)-1,2,2,10,10,11-hexamethyl-4(sulfomethyl)-8-(sulfonatomethyl)-2,10-dihydro-1H-13-oxa-1,11-diazapentacen-11-ium | CC1(C=C(C2=CC3=C(C=C2N1C)OC4=CC5=[NH+]C(C=C(C5=CC4=C3C6=C(C=C(C=C6)C(=O)ON7C(=O)CCC7=O)C(=O)O)CS(=O)(=O)[O-])(C)C)CS(=O)(=O)O)C |
| Alexa Fluor 594 para-isomer | [6-(2-carboxy-5-{[(2,5-dioxopyrrolidin-1-yl)oxy]carbonyl}phenyl)-1,2,2,10,10,11-hexamethyl-8(sulfomethyl)-10,11-dihydro-2H-pyrano[3,2-g:5,6-g']diquinolin-1-ium-4-yl]methanesulfonate | [6-(2-carboxy-5-{[(2,5-dioxopyrrolidin-1-yl)oxy]carbonyl}phenyl)-1,2,2,10,10,11-hexamethyl-4(sulfomethyl)-8-(sulfonatomethyl)-2,10-dihydro-1H-13-oxa-1,11-diazapentacen-11-ium | CC1(C=C(C2=CC3=C(C=C2N1C)OC4=CC5=[NH+]C(C=C(C5=CC4=C3C6=C(C=CC(=C6)C(=O)ON7C(=O)CCC7=O)C(=O)O)CS(=O)(=O)[O-])(C)C)CS(=O)(=O)O)C |
| Alexa Fluor 610-X | bis(N,N-diethylethanaminium) 2,3,5-trichloro-4-{[2-({6-[(2,5-dioxopyrrolidin-1-yl)oxy]-6-oxohexyl}amino)-2-oxoethyl]sulfanyl}-6-[1,2,2,10,10,11-hexamethyl-4,8-bis(sulfonatomethyl)-10,11-dihydro-2H- | 6-(2-carboxylato-3,4,6-trichloro-5-{[({6-[(2,5-dioxopyrrolidin-1-yl)oxy]-6-oxohexyl}carbamoyl)rnethyl]sulfanyl)phenyl)-1,2,2,10,10,11-hexamethyl-4,8-bis(sulfonatomethyl)-2,10-dihydro-1H-13-oxa-1,11-diazapentacen-11-ium; bis(triethylazanium} | CC[NH+](CC)CC.CC[NH+](CC)CC.CC1(C=C(C2=CC3=C(C=C2N1C)OC4=CC5=[NH+](C(C=C(C5=CC4=C3C6=C(C(=C(C(=C6Cl)SCC(=O)NCCCCCC(=O)ON7C(=O)CCC7=O)Cl)Cl)C(=O)[O-])CS(=O)(=O)[O-])(C)C)CS(=O)(=O)[O-])C |

TABLE 1-1-continued

| Product name | Synonym | IUPAC name | Canonical SMILES/Isomeric SMILES |
|---|---|---|---|
| | | pyrano[3,2-g:5,6-g']diquinolin-1-ium-6-yl]benzoate | |
| Alexa Fluor 647 | N/A | 2-[5-[3,3-dimethyl-5-sulfo-1-(3-sulfopropyl)indol-1-ium-2-yl]penta-2,4-dienylidene]-3-methyl-3-[5-oxo-5-(6-phosphonooxyhexylamino)pentyl]-1-(3-sulfopropyl)indole-5-sulfonic acid | CC1(C2=C(C=CC(=C2)S(=O)(=O)O)[N+](=C1C=CC=CC=C3C(C4=C(N3CCCS(=O)(=O)O)C=CC(=C4)S(=O)(=O)O)(C)CCCCC(=O)NCCCCCCO[P+](O)(O)[O-])CCCS(=O)(=O)O)C |
| Atto 425 | 4-[3-(ethoxycarbonyl)-6,8,8-trimethyl-2-oxo-7,8-dihydro-2H-pyrano[3,2-g]quinolin-9(6H)-yl]butanoic acid | 4-[3-(ethoxycarbonyl)-6,8,8-trimethyl-2-oxo-6,7-dihydropyrano[3,2-g]quinolin-9-yl]butanoic acid | CCOC(=O)C1=CC2=CC3=C(C=C2OC1=O)N(C(CC3C)(C)C)CCCC(=O)O |
| Atto 465 | N/A | 4-(3-amino-6-iminoacridin-10-yl)butanoic acid; perchloric acid | C1=CC(=N)C=C2C1=CC3=C(N2CCCC(=O)O)C=C(C=C3)N.OCl(=O)(=O)=O |
| Atto 488 | 10-(3-carboxypropyl)-3,6-bis(dimethylamino)acridinium perchlorate | 4-[3,6-bis(dimethylamino)acridin-10-ium-10-yl]butanoic acid; perchlorate | CN(C)C1=CC2=C(C=C1)C=C3C=CC(=CC3=[N+]2CCCC(=O)O)N(C)C.[O-]Cl(=O)(=O)=O |
| Atto 520 | N-[9-(2-carboxyethyl)-6-(ethylamino)-2,7-dimethyl-3H-xanthen-3-ylidene]ethanaminium perchlorate | [9-(2-carboxyethyl)-6-(ethylamino)-2,7-dimethylxanthen-3-ylidene)-ethylazanium; perchlorate | CCNC1=C(C=C2C(=C1)OC3=CC(=N[NH+]CC)C(=C3C=C2CCC(=O)O)C).[O-]Cl(=O)(=O)=O |
| Atto 532 | N/A | 4[[2-[3-(ethylamino)-6-ethylimino-4,5-disulfoxanthen-9-yl]benzoyl]-methylamino]butanoio acid | CCNC1=C(C2=C(C=C1)C(=C3C=CC(=NCC)C(=C3O2)S(=O)(=O)O)C4=CC=CC=C4C(=O)N(C)CCCC(=O)O)S(=O)(=O)O |
| Atto 610 | 1-(3-carboxypropyl)-9-(dimethylamino)-11,11-dimethyl-2,3,4,11-tetrahydronaphtho[2,3-g]quinolinium perchlorate | 4-[9-(dimethylamino)-11,11-dimethyl-3,4-dihydro-2H-naphtho[2,3-g]quinolin-1-ium-1-yl]butanoic acid; perchlorate | CC1(C2=CC3=[NH+](CCCC3=CC2=CC4=C1C=C(C=C4)N(C)C)CCCC(=O)O)C.[O-]Cl(=O)(=O)=O |
| Atto 635 | 1-(3-carboxypropyl)-9-(dimethylamino)-2,2,4,11,11-dihydronaphtho[2,3-g]quinolinium perchlorate | 4-[9-(dimethylamino)-2,2,4,11,11-pentamethylnaphtho[2,3-g]quinolin-1-ium-1-yl]butanoic acid; perchlorate | CC1=CC([N+](=C2C1=CC3=CC4=C(C=C(C=C4)N(C)C)C(C3=C2)(C)C)CCCC(=O)O)(C)C.[O-]Cl(=O)(=O)=O |
| Atto 655 | N/A | 1-(3-carboxypropyl)-11-ethyl-2,2-dimethyl-4-(sulfonamethyl)-2,3,4,8,9,10-hexahydro-1H-13-oxa-1,6,11-triazapentacen-11-ium | CC[N+]1=C2C=C3C(=NC4=C(O3)C=C5C(=C4)C(CC(N5CCCC(=O)O)(C)C)CS(=O)(=O)[O-])C=C2CCC1 |
| Cy3 | 2-((1E,3E)-3-(1-(5-carboxypentyl)-3,3-dimethyl-5-sulfoindolin-2-ylidene)prop-1-en-1-yl)-1-ethyl-3,3-dimethyl-3H-indol-1-ium-5-sulfonate | (2Z)-2-[(E)-3-[1-(5-carboxypentyl)-3,3-dimethyl-5-sulfoindol-1-ium-2-yl]prop-2-enylidene]-1-ethyl-3,3-dimethylindole-5-sulfonate | CCN\1C2=C(C=C(C=C2)S(=O)(=O)[O-])C(/C1=C/C=C/C3=[N+](C4=C(C3(C)C)C=C(C=C4)S(=O)(=O)O)CCCCCC(=O)O)(C)C |
| Cy3.5 | Cy3.5 carboxylic acid | 6-[(2E)-1,1-dimethyl-2-[(E)-3-( 1,1,3-trimethylbenzo[e]indol-3-ium-2-yl)prop-2-enylidene]benzo[e]indol-3-yl]hexanoic acid; chloride | CC1(C(=[N+](C2=C1C3=CC=CC=C3C=C2)C)/C=C/C=C/4\C(C5=C(N4CCCCCC(=O)O)C=CC6=CC=CC=C65)(C)C)C.[Cl-] |
| Cy5 | 2-((1E,3E,5E)-5-(1-(5-carboxypentyl)-3,3-dimethyl-5-sulfoindolin-2-ylidene)penta-1,3-dien-1-yl)-1-ethyl-3,3-dimethyl-3H-indol-1-ium-5-sulfonate | (2Z)-2-[(2E,4E)-5-[1-(5-carboxypentyl)-3,3-dimethyl-5-sulfoindol-1-ium-2-yl]penta-2,4-dienylidene]-1-ethyl-3,3-dimethylindole-5-sulfonate | CCN\1C2=C(C=C(C=C2)S(=O)(=O)[O-]C(/C1=C/C=C/C=C/C3=[N+](C4=C(C3(C)C)C=C(C=4)S(=O)(=O)O)CCCCCC(=O)O)(C)C |
| Cy5.5 | N/A | (2Z)-2-[(2E,4E)-5-[3-(5-carboxypentyl)-1,1-dimethyl-6,8-disulfabenzo[e]indol-3-ium-2-yl]penta-2,4-dienylidene]-3-ethyl-1,1-dimethyl-8-(trioxidanylsulfanyl)benzo[e]indole-6-sulfonate | CCN\1C2=C(C3=CC(=CC=C3C=C2)S(=O)(=O)[O-])SOOO)C(/C1=C/C=C/C=C/C4=[N+](C5=C(C4(C)C)C6=CC=CC(=C6C=C5)S(=O)(=O)O)CCCCCC(=O)O)(C)C |
| Digoxigenin | Lanadigenin | 3-[(3S,5R,8R,9S,10S,12R,13S,14S,17R)-3,12,14-trihydroxy-10,13-dimethyl-1,2,3,4,5,6,7,8,9,11,12,15,16,17-tetradecahydrocyclopenta[a]phenanthren-17-yl]-2H-furan-5-one | C[C@]12CC[C@@H]([C[C@H]1CC[C@@H]3[C@@H]2C[C@H]([C@]4[C@@]3(CC[C@@H]4C5=CC(=O)OC5)O)C)O)O |
| FITC | Fluorescein 5 isothiocyanate | 3',6'-dihydroxy-6-isothiocyanatospiro[2-benzofuran-3,9'-xanthene]-1-one | C1=CC2=C(C=C1N=C=S)C(=O)OC23C4=C(C=C(C=C4)OC5=C3C=CC(=C5)O |
| TAMRA | Tetramethylrhodamine | 2-[3-(dimethylamino)-6-dimethylazaniumylidenexanthen-9-yl]benzoate | CN(C)C1=CC2=C(C=C1)C(=C3C=CC(=[N+](C)C)C=C3O2)C4=CC=CC=C4C(=O)[O-] |

TABLE 1-1-continued

| Product name | Synonym | IUPAC name | Canonical SMILES/Isomeric SMILES |
|---|---|---|---|
| Texas Red | sulforhodamine sulfonyl chloride | 16-[4-(chlorosulfonyl)-2-sulfonatophenyl]-3-oxa-9$\lambda^5$,23-diazaheptacyclo [17.7,1.1$^{5,9}$.0$^2$,$^{17}$.0$^{4,15}$.0$^{22,27}$.0$^{13,28}$] octacosa-1,4,9(28),13,15,17,19(27)-heptaen-9-ylium | C1CC2=C3C(=C4C(=C2)C(=C5C=C6CCC[N+]7=C6C(=C5O4)CCC7)C8=C(C=C(C=C8)S(=O)(=O)Cl)S(=O)(=O)[O-])CCCN3C1 |

In the method of the present invention, cation-exchange chromatography or anion-exchange chromatography can be selected as ion-exchange chromatography in consideration of an isoelectric point of a substance to be measured, pH and salt concentration of an eluent (also referred to as a mobile phase), etc. In the case of a substance to be measured having a negative charge such as a nucleic acid, anion-exchange chromatography is preferably used.

As used herein, "nucleic acid" is a generic term for ribonucleic acid (hereinafter also referred to as RNA) and deoxyribonucleic acid (hereinafter also referred to as DNA) and means nucleotides composed of bases, sugars, and phosphates (phosphoric acids) linked by phosphodiester bonds. In the present invention, the nucleic acid to be extracted may be either DNA or RNA and may be a target of extraction regardless of whether the nucleic acid is fragmented or not. The nucleic acid may be derived from animals, plants, any organisms including microorganisms, and viruses; however, the origin of the nucleic acid is not limited thereto. The nucleic acid may be a nucleic acid in the cell nucleus or an extranuclear nucleic acid retained by organelles represented by mitochondria, chloroplast, nucleolus, etc. Furthermore, the nucleic acid may be an artificially synthesized nucleic acid or may be a plasmid or a viral vector commonly used as a vector. The preferable nucleic acid for the method of the present invention can be exemplified by a double-stranded deoxyribonucleic acid, and the more preferable nucleic acids can be exemplified by a double-stranded deoxyribonucleic acid having a base sequence with single nucleotide polymorphism, point mutation, and/or deletion/insertion mutation.

A method of PCR amplification is not particularly limited and can be implemented by using a known method appropriately selected depending on a sequence, a length, an amount, etc. of an amplification target. A chain length of a PCR amplification product can appropriately be selected in consideration of factors such as shortening of PCR amplification time, shortening of time of analysis by ion-exchange chromatography, maintenance of separation performance, etc. For example, an upper limit of the chain length of the PCR amplification product is 1000 bp or less, 700 bp or less, 600 bp or less, 500 bp or less, 400 bp or less, 300 bp or less, 200 bp or less, 190 bp or less, 180 bp or less, 170 bp or less, 160 bp or less, 150 bp or less, 140 bp or less, 130 bp or lessor 120 bp or less. In another embodiment, an upper limit of the chain length of the PCR amplification product is 110 bp or less, 100 bp or less, 90 bp or less, 80 bp or less, 70 bp or less, 60 bp or less, or 50 bp or less. On the other hand, a lower limit of the chain length of the PCR amplification product is 30 bp or more, or 40 bp or more. In another embodiment, a lower limit of the chain length of the PCR amplification product is 40 bp or more, 50 bp or more, 60 bp or more, 70 bp or more, 80 bp or more, 90 bp or more, 100 bp or more, or 110 bp or more. In another preferable embodiment, the chain length of the PCR amplification product is 40 bp or more and 120 bp or less.

The single nucleotide polymorphism, point mutation, and/or deletion/insertion mutation detectable by the method of the present invention can be exemplified by a UGT1A1*28 polymorphism (rs8175347), a UGT1A1*6 polymorphism (rs4148323), a JAK2 1849G>T (V617F) mutation site (rs77375493), an MPL 1589G>T (W515L) mutation site (rs121913615), and an MPL 1588: 1599TG>AA (W515K) mutation site (rs121913616).

BRIEF DESCRIPTION OF DRAWINGS

FIG. 1 shows a result of overlaying elution peaks of amplification products according to three fluorescently-labelled primers (SEQ ID NOs: 3, 7, and 8).

FIG. 2 shows separation and detection of amplification products from *6 polymorphic sites of the UGT1A1 gene using non-nucleotide component-added ASPs.

FIG. 3 shows separation and detection of amplification products from a periphery of the codon 515 site of the MPL gene using non-nucleotide component-added ASPs.

EXAMPLES

The present invention will hereinafter be described in detail with examples; however, the present invention is not limited to the following examples.

[Example 1] Amplification Product from *6 Polymorphic Site of UGT1A1 Gene Using Non-Nucleotide Component-Added ASPs The inventors prepared an ASP (SEQ ID NO: 1) having a mismatched base incorporated at only one position in the *6 allele (211G>A) of the human UGT1A1 gene and capable of specifically amplifying from the allele and a reverse primer thereof (SEQ ID NO: 12) (consigned to Sigma-Aldrich) and further separately prepared primers modified with non-nucleotide components at the 5' end of the ASP (SEQ ID NO: 2 was consigned to Thermo Fisher, SEQ ID NO: 8 was consigned to Eurofins Genomics, SEQ ID NOs: 4 and 6 were consigned to Integrated DNA Technologies MBL, and the others were consigned to Sigma Aldridge). Table 2 shows SEQ ID numbers, primer sequences, oligonucleotide length (bp), types of the non-nucleotide components, and excitation wavelength and fluorescence wavelength (nm) of the non-nucleotide components. In Examples 1 to 3, "Alexa488" denotes a mixture of "Alexa Fluor 488 meta-isomer" and "Alexa Fluor 488 para-isomer" of Table 1; "FAM" denotes "5-FAM" of Table 1; "ATTO488" denotes "ATTO 488" of Table 1; "Cy3" denotes "Cy3" of Table 1; "Alexa546" denotes "Alexa Fluor 546" of Table 1; "TAMRA" denotes "TAMRA" of Table 1; "Cy3.5" denotes "Cy3.5" of Table 1; "Cy5" denotes "Cy5" of Table 1; "Cy5.5" denotes "Cy5.5" of Table 1; and "DIG" denotes "Digoxigenin" of Table 1.

TABLE 2

| SEQ ID | 5' to 3' primer sequences | Bases (bp) | Non-nucleotide components | Excitation wavelength (nm) | Fluorescence wavelength (nm) |
|---|---|---|---|---|---|
| | (Forward primers) | | | | |
| 1 | GTTGTACATC AGAGACATA | 19 | Unlabeled | — | — |
| 2 | Alexa488- GTTGTACATC AGAGACATA | 19 | Alexa 488 | 490 | 519 |
| 3 | FAM- GTTGTACATC AGAGACATA | 19 | FAM | 495 | 520 |
| 4 | ATTO488- GTTGTACATC AGAGACATA | 19 | ATTO 488 | 502 | 522 |
| 5 | Cy3- GTTGTACATC AGAGACATA | 19 | Cy3 | 552 | 570 |
| 6 | Alexa546- GTTGTACATC AGAGACATA | 19 | Alexa 546 | 556 | 573 |
| 7 | TAMRA- GTTGTACATC AGAGACATA | 19 | TAMRA | 565 | 580 |
| 8 | Cy3.5- GTTGTACATC AGAGACATA | 19 | Cy3.5 | 581 | 596 |
| 9 | Cy5- GTTGTACATC AGAGACATA | 19 | Cy5 | 643 | 667 |
| 10 | Cy5.5- GTTGTACATC AGAGACATA | 19 | Cy5.5 | 675 | 694 |
| 11 | DIG- GTTGTACATC AGAGACATA | 19 | DIG | — | — |
| | (Common reverse primer) | | | | |
| 12 | GAATCATTCTCAA AAACATTATGCCC | 19 | Unlabeled | — | — |

Reagents, Amplification Conditions, and Ion-Exchange Chromatography Conditions

The inventors prepared 25 μL of a reaction solution containing the following reagents and performed amplification by a two-step allele-specific PCR with CFX96 (Bio-Rad). A purified DNA used in this study was collected from a person homozygous for the allele of the UGT1A1 gene*6.

TABLE 3

[Reagents]

| | |
|---|---|
| 5× buffer (for Q5) | 5 μL |
| 10 mM dNTP | 0.5 μL |
| each of 10 μM forward primers | 1.25 μL |
| 10 μM reverse primer | 1.25 μL |
| 2000 U/mL Q5 DNA polymerase | 0.25 μL |
| Nuclease-free Water | 11.75 μL |
| DNA specimen (25 ng) | 5 μL |

TABLE 3-continued

[Amplification Conditions]

98° C. for 30 seconds
98° C. for 10 seconds, 58° C. for
20 seconds (40 cycles)

[Ion-Exchange Chromatography Conditions]

HPLC anion ion-exchange resin column:
TSKgelDNA-NPR (TOSOH CORPORATION)
Eluent: 20 mM Tris-HCl(pH 9.0),
0.5-0.7 M NaCl gradient (10 min)
Flow rate: 0.75 mL/min
Column oven: 25° C.
Detector: UV wavelength 260 nm (even non-fluorescent substances are detectable at the selected UV wavelength)

The results are shown in Table 4. Interestingly, it was found that although all the amplification products have a chain length of 117 bp, the products amplified by using the primers labeled with the various non-nucleotide components show various patterns of shortened and delayed elution time (also referred to as retention time) of ion-exchange chromatography as compared to the unlabeled amplification product. FIG. 1 exemplifies a result of overlaying elution peaks of amplification products by three fluorescently-labelled primers (SEQ ID NOs: 3, 7, and 8) having particularly significant changes in elution time. This result supports the finding that multiplex analysis of a plurality of mutations can be performed in one ion-exchange chromatographic separation by changing a labeling non-nucleotide component for each specific primer for identifying genetic polymorphism or gene mutation having several patterns at the same site even if the amplification products have the same chain length.

TABLE 4

| | Elution time (min) | Δ min |
|---|---|---|
| ATTO488 | 8.51 | −0.22 |
| Cy3 | 8.53 | −0.19 |
| TAM RA | 8.54 | −0.18 |
| DIG | 8.63 | −0.09 |
| Cy5 | 8.64 | −0.08 |
| Unlabeled | 8.73 | — |
| Alexa488 | 8.83 | 0.10 |
| Alexa548 | 8.93 | 0.20 |
| Cy3.5 | 9.07 | 0.34 |
| FAM | 9.28 | 0.55 |
| Cy5.5 | 9.50 | 0.78 |

[Example 2] Separation and Detection of Amplification Products from *6 Polymorphic Site of UGT1A1 Gene Using Non-Nucleotide Component-Added ASPs SEQ ID NO: 3 described in Example 1 was used as a primer for *6 allele detection. On the other hand, for a primer for wild-type detection at the *6 polymorphic site, an ASP (SEQ ID NO: 13) capable of specifically amplifying from the wild type was separately prepared with a mismatched base introduced at one position without a label as in SEQ ID NO: 1 described in Example 1. Purified DNAs used in this study were collected from persons having the wild type alleles as well as persons heterozygous and homozygous for the allele of the polymorphic site*6 of the UGT1A1 gene.

SEQ ID NO: 13

5'-GTTGTACATCAGAGACGAA-3'

Reagents, Amplification Conditions, and Ion-Exchange Chromatography Conditions

The inventors prepared 25 μL of a reaction solution containing the following reagents and performed amplification by a two-step allele-specific PCR with CFX96 (Bio-Rad). Measurement by ion-exchange chromatography was performed by using the same conditions as Example 1.

TABLE 5

| [Reagents] | |
| --- | --- |
| 5× buffer (for Q5) | 5 μL |
| 10 mM dNTP | 0.5 μL |
| 10 μM forward primer (SEQ ID NO: 3) | 1.25 μL |
| 10 μM reverse primer (SEQ ID NO: 13) | 1.25 μL |
| 10 μM reverse primer | 1.25 μL |
| 2000 U/mL Q5 DNA polymerase | 0.25 μL |
| Nuclease-free Water | 10.5 μL |
| DNA specimen (25 ng) | 5 μL |

The results are shown in FIG. 2. For Specimen 1 heterozygous for *6 allele, two elution peaks were recognized at an elution position of an unlabeled amplification product (around the elution time of 8.6 minutes) and an elution position of a FAM-labeled amplification product (the elution time of 9.2 minutes); for Specimen 2 homozygous for *6 allele, an elution peak was observed only at the elution position of the FAM-labeled amplification product; for Specimen 3 of the wild type, an elution peak was observed only at the elution position of the unlabeled amplification product; and therefore, it was found that the genotypes of the *6 polymorphic site of the UGT1A1 gene are easily and accurately distinguishable.

[Example 3] Separation and Detection of MPL Gene Mutations (Codon 515) Using Non-Nucleotide Component-Added ASPs Codon 515 of the MPL gene has three mutation patterns of W515L, W515K, and W515A different from each other in sequence of two bases at 1543rd and 1544th positions. For forward primers, unlabeled ASPs (SEQ ID NOs: 14 to 16) for detecting respective mutated forms were prepared, and a reverse primer (SEQ ID NO: 17) paired therewith was prepared. Separately, ASPs (SEQ ID NOs: 18, 19, 20) were also prepared by adding a non-nucleotide component for W515K. Additionally, plasmid DNAs incorporating respective gene mutation sequences (SEQ ID NO: 21 to 23) were prepared as specimens (consigned to Eurofins Genomics).

(ASP for W515L)
SEQ ID NO: 14
5'-CTGCTGCTGCTGAGGTTTC-3'

(ASP for W515K)
SEQ ID NO: 15
5'-CTGCTGCTGCTGAGGAA-3'

(ASP for W515A)
SEQ ID NO: 16
5'-TGCTGCTGCTGAGCGC-3'

(common reverse primer)
SEQ ID NO: 17
5'-GGCGGTACCTGTAGTGTGC-3'

(ASP for biotin-labeled W515K)
SEQ ID NO: 18
5'-Biotin-CTGCTGCTGCTGAGGAA-3'

(ASP for amino-group-labeled W515K)
SEQ ID NO: 19
5'-NH2-CTGCTGCTGCTGAGGAA-3'

(ASP for Cy3.5 fluorescent-dye-labeled W515K)
SEQ ID NO: 20
5'-Cy3.5-CTGCTGCTGCTGAGGAA-3'

[Chem 1]
(W515L gene mutant sequence)
SEQ ID NO: 21
CAGAGTAGGGGCTGGCTGGATGAGGGCGGGGCTCCGGCCCGGGTGGG

CCGAAGTCTGACCCTTTTTGTCTCCTAGCCTGGATCTCCTTGGTGAC

CGCTCTGCATCTAGTGCTGGGCCTCAGCGCCGTCCTGGGCCTGCTGC

TGCTGAGGTTGCAGTTTCCTGCACACTACAGGTACCGCCCCGCCAG

GCAGGAGACTGGCGGTGGACCAGGTGGAGCCGAAGGCCTGTAAACAG

GCATTCTTGGTTCGCTCTGTGACCCCAGATCTCCGTCCACCGCCCGT

GCGCACCTACGGCTTCGCCACTTCCTGCACGTCA

[Chem 2]
(W515K gene mutant sequence)
SEQ ID NO: 22
CAGAGTAGGGGCTGGCTGGATGAGGGCGGGGCTCCGGCCCGGGTGGG

CCGAAGTCTGACCCTTTTTGTCTCCTAGCCTGGATCTCCTTGGTGAC

CGCTCTGCATCTAGTGCTGGGCCTCAGCGCCGTCCTGGGCCTGCTGC

TGCTGAGGAAGCAGTTTCCTGCACACTACAGGTACCGCCCCGCCAG

GCAGGAGACTGGCGGTGGACCAGGTGGAGCCGAAGGCCTGTAAACAG

GCATTCTTGGTTCGCTCTGTGACCCCAGATCTCCGTCCACCGCCCGT

GCGCACCTACGGCTTCGCCACTTCCTGCACGTCA

[Chem 3]
(W515A gene mutant sequence)
SEQ ID NO: 23
CAGAGTAGGGGCTGGCTGGATGAGGGCGGGGCTCCGGCCCGGGTGGG

CCGAAGTCTGACCCTTTTTGTCTCCTAGCCTGGATCTCCTTGGTGAC

CGCTCTGCATCTAGTGCTGGGCCTCAGCGCCGTCCTGGGCCTGCTGC

TGCTGAGGGCGCAGTTTCCTGCACACTACAGGTACCGCCCCGCCAG

GCAGGAGACTGGCGGTGGACCAGGTGGAGCCGAAGGCCTGTAAACAG

GCATTCTTGGTTCGCTCTGTGACCCCAGATCTCCGTCCACCGCCCGT

GCGCACCTACGGCTTCGCCACTTCCTGCACGTCA

Reagents, Amplification Conditions, and Ion-Exchange Chromatography Conditions

The inventors prepared 25 μL of a reaction solution containing the following reagents and performed amplification by a two-step allele-specific PCR with CFX96 (Bio-Rad).

TABLE 6

| [Reagents] | |
| --- | --- |
| 5× buffer (for Q5) | 5 μL |
| 10 mM dNTP | 0.5 μL |
| 10 μM forward primer (SEQ ID NO: 14) | 1.25 μL |
| 10 μM forward primer | 0.31 μL |

TABLE 6-continued

| | |
|---|---|
| (any of SEQ ID NOs: 15 and 18 to 20) | |
| 10 μM forward primer (SEQ ID NO: 16) | 0.25 μL |
| 10 μM reverse primer (SEQ ID NO: 17) | 1.25 μL |
| 20× EvaGreen | 1.25 μL |
| 2000 U/mL Q5 DNA polymerase | 0.25 μL |
| Nuclease-free Water | 9.94 μL |
| DNA specimen | 5 μL |
| (1500 copies of linear plasmid DNA [SEQ ID NOs: 21 to 23] cleaved by an appropriate restriction enzyme) | |
| [Amplification Conditions] | |

98° C.: 30 seconds
98° C.: 10 seconds, 62° C.: 20 seconds (35 cycles)
[Ion-Exchange Chromatography Conditions]

HPLC anion ion-exchange resin column:
TSKgelDNA-NPR (TOSOH CORPORATION)
Eluent: 20 mM Tris-HCl (pH 9.0),
0.47-0.62M NaCl gradient (10 min)
Flow rate: 0.75 mL/min
Column oven: 25° C.
Detector: UV wavelength 260 nm (even non-fluorescent substances are detectable at the selected UV wavelength)

FIG. 3 shows ion-exchange chromatographic separation and detection results of amplification products from a periphery of the codon 515 site of the MPL gene using non-nucleotide component-added ASPs. First, in the result of ion-exchange chromatographic separation using the unlabeled ASP, the elution position (elution time of 3.82 minutes) of the amplification product (45 bp) of W515A can be distinguished due to a difference from the elution positions of the amplification products of W 515L and W515K (both 46 bp); however, the amplification products of W515L and W515K have almost the same elution positions (elution times of 4.42 minutes and 4.35 minutes), and it was found that although the presence/absence of mutation is confirmed, the pattern thereof cannot be identified. In contrast, the respective elution positions of the amplification products using the W515K non-nucleotide component-added ASPs (SEQ ID NOs: 18, 19, 20) were 4.16 minutes, 3.91 minutes, and 4.97 minutes, and it was confirmed that the elution positions overlap with neither the elution position of W515L nor the elution position of the amplification product of W515A.

This result supports the finding that when the amplification products using ASPs have similar lengths and are indistinguishable with respect to elution positions in separation and detection using ion-exchange chromatography, the separation and detection are enabled by adding a suitable non-nucleotide component to the ASP.

In view of the findings, by adding a plurality of non-nucleotide components changing an elution time in ion-exchange chromatography to a plurality of ASPs and by adding a non-nucleotide component also to a primer paired therewith, the elution time can variously be adjusted. Furthermore, when fluorescent dyes are used as the non-nucleotide components, distinction can also be made according to detected wavelength by selecting those having fluorescent wavelength not causing a crosstalk even if no difference exists in elution time.

A method for detecting amplification products can be not only a method in which a reagent subjected to an amplification reaction is directly separated by ion-exchange chromatography but also a method in which multiple amplified reagents are separately prepared before a mixed solution thereof is separated by ion-exchange chromatography.

INDUSTRIAL APPLICABILITY

Therefore, the present invention provides a method that enables easy and accurate detection of genotypes and single base substitutions of multiple genetic polymorphisms, which are difficult to detect with conventional methods, and that can support multiplexing of genetic testing recently in rising demand.

The invention claimed is:

1. A method for detecting a gene mutation comprising a step of discriminating, by using ion-exchange chromatography, two or more kinds of gene amplification products amplified by using two or more kinds of allele specific primers, characterized in that a non-nucleotide component is added to the 5' end of at least one of the two or more kinds of allele specific primers.

2. The detection method according to claim 1, wherein the ion-exchange chromatography is anion-exchange chromatography.

3. The detection method according to claim 1, wherein the non-nucleotide component is a substance inducing a change in electric charge at the 5' end of the primer.

4. A method for detecting the presence of at least one allele at a polymorphic site contained in a double-stranded deoxyribonucleic acid in a sample, comprising the steps of:
 (a) providing a sample containing a double-stranded deoxyribonucleic acid containing a polymorphic site;
 (b) providing a first primer, a second primer, and a third primer, wherein
  the sequence of the first primer is complementary to the second strand of the double-stranded deoxyribonucleic acid having a first allele at the polymorphic site, and any one or two or three out of three bases at the 3' end or one or both of two bases at the 3' end of the sequence of the first primer corresponds to the polymorphism site, wherein
  the sequence of the second primer is complementary to the second strand of the double-stranded deoxyribonucleic acid having a second allele at the polymorphic site, and any one or two or three out of three bases at the 3' end or one or both of two bases at the 3' end of the sequence of the second primer corresponds to the polymorphism site, wherein
  the sequence of the third primer does not include the polymorphic site and is complementary to the first strand of the double-stranded deoxyribonucleic acid, wherein
  a non-nucleotide component is added to at least one of the first primer and the second primer;
 (c) performing a polymerase chain reaction, wherein
  the polymerase chain reaction is performed under a condition that strand elongation due to a polymerase from the first primer hybridized to the second strand of the double-stranded deoxyribonucleic acid having the first allele preferentially occurs as compared to strand elongation due to a polymerase from the second primer hybridized to the second strand of the double-stranded deoxyribonucleic acid having the first allele, and that strand elongation due to a polymerase from the second primer hybridized to the second strand of the double-stranded deoxyribonucleic acid having the second allele preferentially occurs as compared to strand elongation due to a polymerase from the first primer hybridized to the second strand of the double-stranded deoxyribonucleic acid having the second allele;
 (d) subjecting amplification products of the polymerase chain reaction to ion-exchange chromatography, wherein
  the difference in size of the amplification product of the polymerase chain reaction from the first primer and the third primer and the amplification product of the polymerase chain reaction from the second primer and the third primer is 0 base pair, 1 base pair, 2 base pairs, 3 base pairs, 4 base pairs, 5 base pairs, 6 base pairs, 7 base pairs, 8 base pairs, 9 base pairs, or 10 base pairs; and
 (e) detecting the presence of one or both of the first and second alleles based on elution positions or elution times of the amplification products.

5. The method according to claim 4, wherein the step (a) is a step of extracting genomic DNA from a somatic cell specimen of mammals such as human.

6. The method according to claim 4, wherein the polymorphic site is a UGT1A1*28 polymorphism (r58175347), a UGT1A1*6 polymorphism (r54148323), a JAK2 1849G>T (V617F) mutation site (rs77375493), an MPL 1589G>T (W515L) mutation site (r5121913615), or an MPL 1588:1599TG>AA (W515K) mutation site (r5121913616).

7. The method according to claim 4, wherein the non-nucleotide component is a substance inducing a change in electric charge at the 5' end of the primer.

8. The method according to claim 4, wherein the non-nucleotide component is added to the third primer.

9. The detection method according to claim 2, wherein the non-nucleotide component is a substance inducing a change in electric charge at the 5' end of the primer.

10. The method according to claim 5, wherein the polymorphic site is a UGT1A1*28 polymorphism (r58175347), a UGT1A1*6 polymorphism (r54148323), a JAK2 1849G>T (V617F) mutation site (rs77375493), an MPL 1589G>T (W515L) mutation site (r5121913615), or an MPL 1588:1599TG>AA (W515K) mutation site (r5121913616).

11. The method according to claim 5, wherein the non-nucleotide component is a substance inducing a change in electric charge at the 5' end of the primer.

12. The method according to claim 6, wherein the non-nucleotide component is a substance inducing a change in electric charge at the 5' end of the primer.

13. The method according to claim 5, wherein the non-nucleotide component is added to the third primer.

14. The method according to claim 6, wherein the non-nucleotide component is added to the third primer.

15. The method according to claim 7, wherein the non-nucleotide component is added to the third primer.

* * * * *

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gttgtacatc agagacata                                                   19

<210> SEQ ID NO 2
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with Alexa488

<400> SEQUENCE: 2
gttgtacatc agagacata                                                   19

<210> SEQ ID NO 3
```

-continued

```
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with FAM

<400> SEQUENCE: 3
gttgtacatc agagacata                                                  19

<210> SEQ ID NO 4
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with ATTO488

<400> SEQUENCE: 4
gttgtacatc agagacata                                                  19

<210> SEQ ID NO 5
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with Cy3

<400> SEQUENCE: 5
gttgtacatc agagacata                                                  19

<210> SEQ ID NO 6
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with Alexa546

<400> SEQUENCE: 6
gttgtacatc agagacata                                                  19

<210> SEQ ID NO 7
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with TAMRA

<400> SEQUENCE: 7
gttgtacatc agagacata                                                  19
```

```
<210> SEQ ID NO 8
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with Cy3.5

<400> SEQUENCE: 8
gttgtacatc agagacata                                                19

<210> SEQ ID NO 9
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with Cy5

<400> SEQUENCE: 9
gttgtacatc agagacata                                                19

<210> SEQ ID NO 10
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with Cy5.5

<400> SEQUENCE: 10
gttgtacatc agagacata                                                19

<210> SEQ ID NO 11
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: labeled with DIG

<400> SEQUENCE: 11
gttgtacatc agagacata                                                19

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
gaatcattct caaaaacatt atgccc                                        26

<210> SEQ ID NO 13
<211> LENGTH: 19
<212> TYPE: DNA
```

```
<213> ORGANISM: Artificial Sequence
<220> FEATURE:
<223> OTHER INFORMATION: primer

<400> SEQUENCE: 13
gttgtacatc agagacgaa                                                   19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
ctgctgctgc tgaggtttc                                                   19

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
ctgctgctgc tgaggaa                                                     17

<210> SEQ ID NO 16
<211> LENGTH: 16
<212> TYPE: DNA
<213> ORGANISM: Artificial Sequence
<220> FEATURE:
<223> OTHER INFORMATION: primer

<400> SEQUENCE: 16
tgctgctgct gagcgc                                                      16

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
ggcggtacct gtagtgtgc                                                   19

<210> SEQ ID NO 18
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: Biotin

<400> SEQUENCE: 18
ctgctgctgc tgaggaa                                                     17

<210> SEQ ID NO 19
<211> LENGTH: 17
<212> TYPE: DNA
<213> ORGANISM: Artificial Sequence
<220> FEATURE:
<223> OTHER INFORMATION: primer
```

```
<220> FEATURE:
<221> NAME/KEY: misc_feature
<222> LOCATION: (1)..(1)
<223> OTHER INFORMATION: NH2

<400> SEQUENCE: 19
ctgctgctgc tgaggaa                                                   17

<210> SEQ ID NO 20
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: Cy3.5

<400> SEQUENCE: 20
ctgctgctgc tgaggaa                                                   17

<210> SEQ ID NO 21
<211> LENGTH: 316
<212> TYPE: DNA
<213> ORGANISM: Artificial Sequence
<220> FEATURE:
<223> OTHER INFORMATION: plasmid
<220> FEATURE:
<221> NAME/KEY: allele
<222> LOCATION: (151)..(151)
<223> OTHER INFORMATION: W515L

<400> SEQUENCE: 21
cagagtaggg gctggctgga tgagggcggg gctccggccc gggtgggccg aagtctgacc     60 cttttttgtct cctagcctgg atctccttgg tgaccgctct gcatctagtg ctgggcctca   120
gcgccgtcct gggcctgctg ctgctgaggt tgcagtttcc tgcacactac aggtaccgcc   180
cccgccaggc aggagactgg cggtggacca ggtggagccg aaggcctgta aacaggcatt   240
cttggttcgc tctgtgaccc cagatctccg tccaccgccc gtgcgcacct acggcttcgc   300
cacttcctgc acgtca                                                   316

<210> SEQ ID NO 22
<211> LENGTH: 316
<212> TYPE: DNA
<213> ORGANISM: Artificial Sequence
<220> FEATURE:
<223> OTHER INFORMATION: plasmid
<220> FEATURE:
<221> NAME/KEY: allele
<222> LOCATION: (150)..(151)
<223> OTHER INFORMATION: W515K

<400> SEQUENCE: 22
cagagtaggg gctggctgga tgagggcggg gctccggccc gggtgggccg aagtctgacc     60 cttttttgtct cctagcctgg atctccttgg tgaccgctct gcatctagtg ctgggcctca   120
gcgccgtcct gggcctgctg ctgctgagga agcagtttcc tgcacactac aggtaccgcc   180
cccgccaggc aggagactgg cggtggacca ggtggagccg aaggcctgta aacaggcatt   240
cttggttcgc tctgtgaccc cagatctccg tccaccgccc gtgcgcacct acggcttcgc   300
cacttcctgc acgtca                                                   316

<210> SEQ ID NO 23
```

```
<211> LENGTH: 316
<212> TYPE: DNA
<213> ORGANISM: Artificial Sequence
<220> FEATURE:
<223> OTHER INFORMATION: primer
<220> FEATURE:
<221> NAME/KEY: allele
<222> LOCATION: (150)..(151)
<223> OTHER INFORMATION: W515A

<400> SEQUENCE: 23
cagagtaggg gctggctgga tgagggcggg gctccggccc gggtgggccg aagtctgacc      60 cttttgtct cctagcctgg atctccttgg tgaccgctct gcatctagtg ctgggcctca     120
gcgccgtcct gggcctgctg ctgctgaggg cgcagtttcc tgcacactac aggtaccgcc    180
cccgccaggc aggagactgg cggtggacca ggtggagccg aaggcctgta aacaggcatt    240
cttggttcgc tctgtgaccc cagatctccg tccaccgccc gtgcgcacct acggcttcgc    300
cacttcctgc acgtca                                                    316
```